(12) United States Patent
Priske et al.

(10) Patent No.: US 9,713,791 B2
(45) Date of Patent: Jul. 25, 2017

(54) MEMBRANE CASCADE WITH FALLING SEPARATION TEMPERATURE

(71) Applicant: EVONIK DEGUSSA GMBH, Essen (DE)

(72) Inventors: Markus Priske, Mobile, AL (US); Robert Franke, Marl (DE); Bart Hamers, VG Horst (NL); Patrick Schmidt, Dortmund (DE); Andrzej Górak, Witten (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/908,037

(22) PCT Filed: Jul. 25, 2014

(86) PCT No.: PCT/EP2014/066028
§ 371 (c)(1),
(2) Date: Jan. 27, 2016

(87) PCT Pub. No.: WO2015/014741
PCT Pub. Date: Feb. 5, 2015

(65) Prior Publication Data
US 2016/0158703 A1    Jun. 9, 2016

(30) Foreign Application Priority Data

Jul. 31, 2013 (DE) ............ 10 2013 215 004

(51) Int. Cl.
| C07C 45/50 | (2006.01) |
| B01D 61/58 | (2006.01) |
| B01D 61/02 | (2006.01) |
| B01D 61/12 | (2006.01) |

(52) U.S. Cl.
CPC ............ *B01D 61/58* (2013.01); *B01D 61/022* (2013.01); *B01D 61/027* (2013.01); *B01D 61/12* (2013.01); *C07C 45/50* (2013.01); *B01D 2311/04* (2013.01); *B01D 2311/08* (2013.01); *B01D 2311/106* (2013.01); *B01D 2311/25* (2013.01); *B01D 2317/025* (2013.01); *B01D 2317/027* (2013.01)

(58) Field of Classification Search
CPC ........................... C07C 45/50; B01D 2311/00
USPC ................... 568/454; 210/184, 650
See application file for complete search history.

(56) References Cited

U.S. PATENT DOCUMENTS

| 5,174,899 A | 12/1992 | Bahrmann et al. |
| 5,240,471 A | 8/1993 | Barbe et al. |
| 5,538,536 A | 7/1996 | Fuentes et al. |
| 5,773,667 A | 6/1998 | Bahrmann et al. |
| 8,226,829 B2 | 7/2012 | Wiese et al. |
| 8,748,643 B2 | 6/2014 | Priske et al. |
| 8,969,628 B2 | 3/2015 | Priske et al. |
| 8,999,038 B2 | 4/2015 | Ungerank et al. |
| 9,149,780 B2 | 10/2015 | Hamers et al. |
| 9,353,040 B2 | 5/2016 | Baumgarten et al. |
| 2006/0237361 A1 | 10/2006 | Dudziak et al. |
| 2015/0299079 A1 | 10/2015 | Fridag et al. |
| 2015/0336078 A1 | 11/2015 | Hamers et al. |
| 2016/0002136 A1 | 1/2016 | Lueken et al. |
| 2016/0082393 A1 | 3/2016 | Priske et al. |

FOREIGN PATENT DOCUMENTS

| CN | 101591254 A | 12/2009 |
| DE | 102009001225 | 9/2010 |
| DE | 102012223572 | 6/2014 |
| DE | 102013208759 | 11/2014 |
| EP | 0374615 | 6/1990 |
| EP | 0823282 | 2/1998 |
| EP | 0781166 | 8/2000 |
| EP | 1931472 | 1/2009 |
| EP | 1603663 | 5/2010 |
| EP | 2226113 | 9/2010 |
| EP | 2401078 | 10/2016 |
| WO | 2013034690 | 3/2013 |
| WO | 2014/183952 | 11/2014 |
| WO | 2015/058919 A1 | 4/2015 |
| WO | 2015/086634 A1 | 6/2015 |
| WO | 2015/113840 | 8/2015 |

OTHER PUBLICATIONS

International Search Report for PCT/EP2014/066028 dated Feb. 5, 2015 (German with English translation) 7 pages.
Written Opinion of the International Searching Authority for PCT/EP2014/066028 dated Feb. 5, 2015 (German with English translation) 7 pages. 10. pages.

(Continued)

*Primary Examiner* — Sikarl Witherspoon
(74) *Attorney, Agent, or Firm* — Smith, Gambrell & Russell, LLP (57) ABSTRACT

The invention relates to a process for separating a composition of matter with the aid of a membrane cascade having at least two stages, in which a separation is effected in each stage at at least one membrane at a separation temperature set for the particular stage. The invention further relates to a corresponding membrane cascade, to the use of said membrane cascade for catalyst separation from homogeneously catalyzed mixtures, and to a process for hydroformylation, in which the catalyst is separated by means of a membrane cascade. The problem addressed thereby is that of specifying a membrane-based process for separating compositions of matter, which has a minimum membrane area requirement and nevertheless fulfills the separation task and separation performance required. This problem is solved by the use of a membrane cascade with falling separation temperature.

17 Claims, 9 Drawing Sheets

(56) References Cited

OTHER PUBLICATIONS

Lin; Justin Chun-Te & Livingston, Andrew G.. Nanofiltration membrane cascade for continuous solvent exchange. Chemical Engineering Science, Apr. 22, 2007 Oxford, GB—ISSN 0009-2509. vol. 62, Nr:10, pp. 2728-2736. (abstract provided).

Siew, Weiming Eugene; Livingston, Andrew G; Ates, Célal; & Merschaert, Alain. Molecular separation with an organic solvent nanofiltration cascade—augmenting membrane selectivity with process engineering. Chemical Engineering Science, Mar. 1, 2013 Pergamon—ISSN 0009-2509. vol. 90, pp. 299-310. (abstract provided).

International Preliminary Report on Patentability for PCT/EP2014/066028 dated Jun. 23, 2015 (13 pages).

MEMBRANE CASCADE WITH FALLING SEPARATION TEMPERATURE

The invention relates to a process for separating a composition of matter with the aid of a membrane cascade having at least two stages, in which a separation is effected in each stage at at least one membrane at a separation temperature set for the particular stage. The invention further relates to a corresponding membrane cascade, to the use of said membrane cascade for catalyst separation from homogeneously catalysed mixtures, and to a process for hydroformylation, in which the catalyst is separated by means of a membrane cascade.

The chemical engineer understands a separating operation to mean a measure for qualitative separation of compositions of matter in which an input composition of matter comprising a plurality of components is converted to at least two output compositions of matter, the output compositions of matter obtained having a different quantitative composition from the input composition of matter. The output compositions of matter obtained generally have a particularly high concentration of the desired component, in the best case being pure products. There is usually a conflict, in terms of objectives, of purification level or separation sharpness with the throughput and the required apparatus complexity and the energy input.

Figure 1:
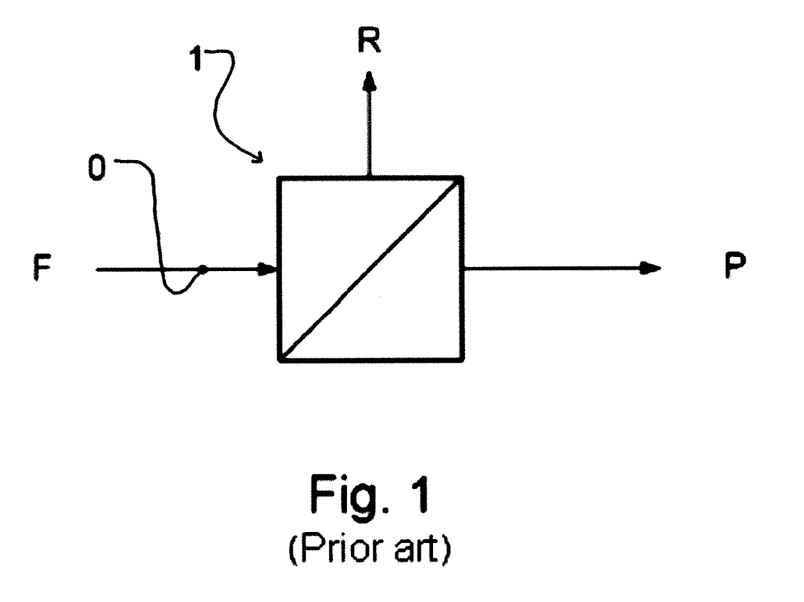
FIG. 1 shows a simple membrane process according to the prior art.

In what are called membrane separation processes, the composition of matter 0 to be separated is applied as feed F a membrane 1 which has a different permeability for the components present in the composition of matter 0. Components which pass through the membrane 1 particularly efficiently are collected as permeate P beyond the membrane 1 and conducted away. Components which are preferentially retained by the membrane 1 are collected as retentate R on the same side of the membrane 1 and conducted away.

The positions of the streams at a membrane are apparent from FIG. 1.

FIG. 1: simple membrane process (prior art)

In membrane technology, different separation effects come to bear. More particularly, not just differences in the size of the components (mechanical sieving effect) but also the dissolution and diffusion effects are utilized. The less permeable the separation-active layer of the membrane becomes, the more dominant the dissolution and diffusion effects become. The separation characteristics of a membrane are therefore not entirely compatible to those of a simple filter which makes use merely of the sieving effect.

An excellent introduction into membrane technology is given by:

Melin/Rautenbach: Membranverfahren, Grundlagen der Modul- und Anlagenauslegung [Membrane Processes, Principles of Module and System Design], Springer, Berlin Heidelberg 2004.

One advantage of the membrane processes over other separation processes is the low energy requirement. Thus, generally only mechanical power is required to operate pumps to maintain the required flow rates and pressures. Unlike thermal separation processes, for instance, membrane separation processes do not require any thermal energy.

It is a specific disadvantage of membrane separation processes that this still comparatively young technology stands and falls with the availability of the membranes. Thus, the effective separation of specific components from the composition of matter often requires a specific membrane material which is not always available in sufficiently large amounts or is even unknown. The separation of large stream volumes, however, requires very large membrane areas and a correspondingly large amount of material and high capital costs.

This is all the more true if a particularly high retention of a particular component is required:

Retention is a measure of the ability of a membrane to enrich a component present in the feed in the retentate, or to deplete it in the permeate. The retention R is calculated from the molar proportion of the component in question on the permeate side of the membrane $x_P$ and the molar proportion of the component in question on the retentate side of the membrane $x_R$, as follows:

$$R = 1 - x_P/x_R$$

These concentrations $x_P$ and $x_R$ should be measured directly on the two sides of the membrane. If the membrane has a low retention with respect to the component to be retained for instance because no more effective membrane material is known—the composition stream to be separated has to be applied repeatedly to the membrane in order to achieve sufficient retention overall. This is accomplished either by recycling the permeate into the feed to the same membrane or by feeding a second membrane with the permeate from the first membrane.

A membrane separation process in which the composition stream to be separated permeates through a plurality of membranes is called a multistage process. Multistage membrane separation processes are conducted in what are called membrane cascades; these are arrangements of a plurality of individual membranes connected to one another in series and/or in parallel. Membrane cascades generally also comprise pumps to maintain the transmembrane pressure required over the membrane as a driving force, and any recycle lines which conduct substreams within the cascade repeatedly through individual stages.

Even though membrane cascades may be of very complex construction, any membrane cascade can be viewed as a black box like an individual membrane, which has the basic feed, retentate and permeate connections shown in FIG. 1. In order to distinguish the flows in the black box from the internal flows of the membrane cascade, reference is made hereinafter to a resulting permeate or resulting retentate when the retentate or permeate of an overall membrane cascade is being discussed.

As already mentioned, a plurality of membranes may be connected in parallel and/or in series within a membrane cascade. This is done quite frequently in industry, since membranes in industry are generally configured as a membrane module with a limited membrane area, and the total area required is provided by means of several membrane modules connected in series.

The parameter of interest for the characterization of a membrane cascade is therefore not the number of membranes within a membrane separation unit but the number of stages. A stage is understood by the membrane specialist to mean a separation step in which a pressure drop occurs over one or more membranes. This pressure drop is the difference between feed and permeate at the membrane in question and is called transmembrane pressure. Without this pressure drop, no separation takes place at the membrane. Since, in a multistage membrane process, the drop in pressure that has occurred after the first stage has to be built up again, the number of stages can also be inferred from the number of pumps for setting or re-establishing the transmembrane pressure. Alternatively, although rarely implemented in practice, the transmembrane pressure difference of two or more stages can also be generated by means of a pump. For this purpose, the pump generates the total transmembrane pressure of two or more stages upstream of one state. In other words, the permeate pressure of the upstream stage constitutes the feed pressure of the downstream stage.

There are two known basic connection forms of membrane cascades, namely the enriching cascade and the stripping cascade. There also exists mixed forms, but these can be traced back to the two basic connections.

Figure 2:
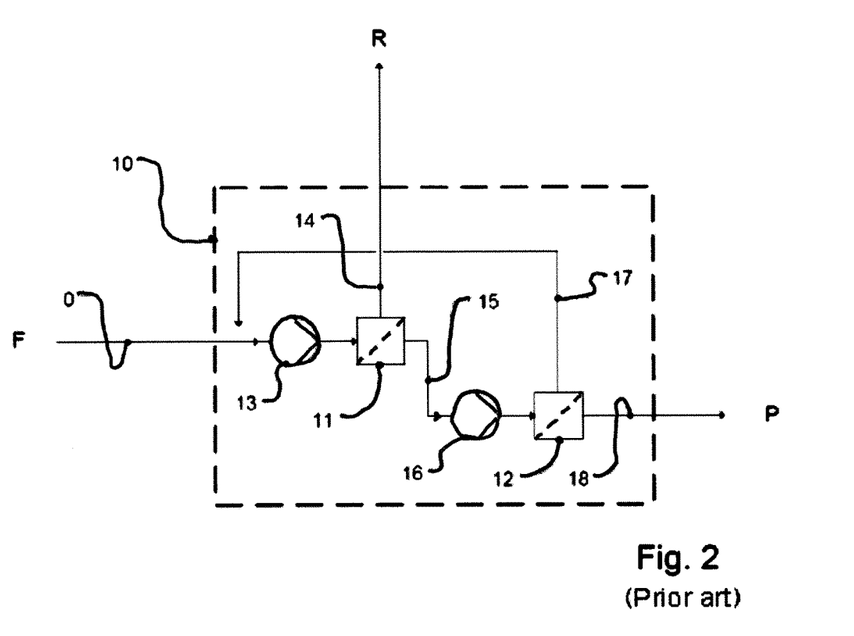
FIG. 2 shows a two-stage enriching cascade according to the prior art.

The construction of an enriching cascade with two membrane separation stages is shown by FIG. 2.

FIG. 2: two-stage enriching cascade (prior art)

The enriching cascade 10 can be viewed as a black box which, like an individual membrane, accepts the composition of matter 0 to be separated as feed F and separates it into a resulting retentate R and a resulting permeate P. The enriching cascade 10 comprises two stages 11, 12 connected in series in the direction of permeate flow, which in turn comprise one or more membranes. The incoming feed F is conveyed by a conveying pump 13 to the first stage 11. A first separation takes place at a membrane therein, such that a retentate from the first stage 14 and a permeate from the first stage 15 are obtained. The retentate from the first stage 14 corresponds to the resulting retentate R from the enriching cascade 10 and is discharged from the separation process.

The permeate 15 from the first stage 11, in contrast, is applied as feed to the second stage 12. In order to compensate for the drop in pressure that has occurred in the first stage 11 (transmembrane pressure), a high-pressure pump 16 is provided between the first and second stages.

In the second stage 12, another separation takes place at at least one membrane, such that a retentate 17 from the second stage and a permeate 18 from the second stage are obtained. The permeate 18 from the second stage has therefore passed through the two stages 11, 12 and consequently has a particularly high purity. It is discharged from the process as the resulting permeate P.

Meanwhile, the retentate 17 from the second stage 12 is recycled into the feed to the first stage 11, in order to be purified again.

Since the resulting permeate P from an enriching cascade 10 has permeated through all the stages 11, 12, enriching cascades serve to enrich a component present in the incoming stream allowed to pass through preferentially by the membranes in the resulting permeate P.

If, in contrast, the aim is to enrich a component retained preferentially by the membrane used in the retentate, a stripping cascade is used.

Figure 3:
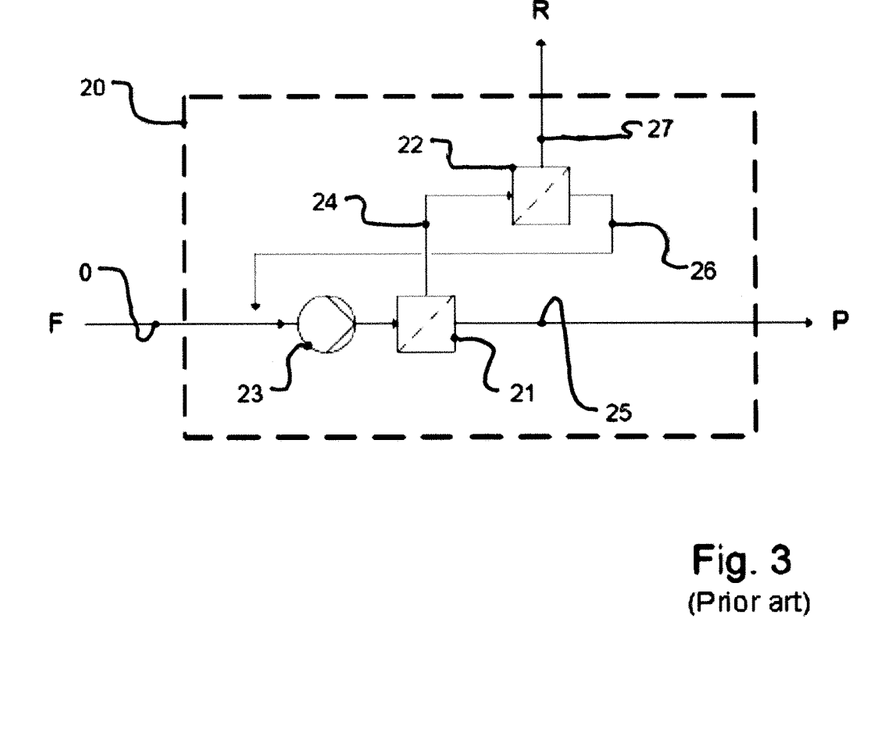
FIG. 3 shows a two-stage stripping cascade according to the prior art.

The construction of a stripping cascade with two membrane separation stages is shown by FIG. 3.

FIG. 3: two-stage stripping cascade (prior art)

The stripping cascade 20 can again be regarded as a black box corresponding to a single membrane which is fed with the incoming stream 0 as feed F, which separates the feed F into a resulting retentate R and a resulting permeate P.

The stripping cascade 20 differs from the enriching cascade 10 shown in FIG. 2 in that the stages are arranged successively in the direction of retentate flow. Separation is effected in the two-stage stripping cascade shown in FIG. 3 by two stages 21, 22.

For the purpose of separation of the stream 0, it is applied to the first stage of the stripping cascade 20 and separated therein into permeate 24 and retentate 25. To generate the necessary transmembrane pressure, a pressure-increasing pump 23 is provided. The permeate 25 of the first stage 21 is discharged from the stripping cascade 20 and thus corresponds to the resulting permeate P.

Meanwhile, the retentate 24 from the first stage 21 is applied as feed to the second stage 22. For this purpose, no pump arranged between the first stage 21 and second stage 22 is required, since the transmembrane pressure drops constantly in the permeate direction, such that the pressure of the retentate 24 apart from flow losses corresponds essentially to that of the feed to the first stage 21.

Within the second stage 22, another separation takes place at at least one membrane. The retentate obtained from the second stage 27 is discharged as resulting retentate R from the stripping cascade 20. Since it has not passed through any membrane in the two stages 21, 22, it is particularly rich in components retained preferentially by the membranes.

Meanwhile, the permeate 26 from the second stage 22 is recycled and added to the feed to the first stage 21. The pressure-increasing pump 23 balances out the drop in pressure experienced by the permeate 26 in the second stage 22.

In the field of desalination, gas separation and pharmaceutical purification, membrane cascades are already widespread.

A comparatively young field of use for membrane cascades, in contrast, is catalyst separation from homogeneously catalysed chemical reactions.

Where a catalytic reaction is discussed here, this means a chemical reaction in which at least one reactant is converted to at least one product in the presence of a catalyst. Reactant and product are referred to collectively as reaction participants. The catalyst is essentially not consumed during the reaction, apart from typical ageing and breakdown phenomena.

The reaction is conducted in a locally delimited reaction zone. In the simplest case, this is a reactor of any design, although it may also be a multitude of reactors connected to one another.

The material withdrawn continuously or discontinuously from the reaction zone is referred to here as reaction mixture. The reaction mixture comprises at least the target product of the reaction. According to the industrial reaction regime, it may also comprise unconverted reactants, more or less desirable further conversion products or accompanying products from further reactions and/or side reactions, and solvents. In addition, the reaction mixture may also comprise the catalyst.

Catalytically conducted chemical reactions can be divided into two groups with regard to the physical state of the catalyst used: mention should be made here firstly of the heterogeneously catalyzed reactions in which the catalyst is present in solid form in the reaction zone and is surrounded by reaction participants. In the case of homogeneous catalysis, in contrast, the catalyst is dissolved in the reaction mixture. Homogeneously dissolved catalysts are usually much more effective in catalytic terms than heterogeneous catalysts.

In any catalytically conducted reaction, it is necessary to separate the catalyst from the reaction mixture. The reason for this is that the catalyst is barely consumed during the reaction and can therefore be reused. Moreover, the catalyst is usually much more valuable than the product produced therewith. Catalyst loss should therefore be avoided if possible.

The catalyst separation can be accomplished in a technically simple manner in the case of heterogeneously catalysed reactions: the solid catalyst simply remains in the reaction zone, while the liquid and/or gaseous reaction mixture is drawn off from the reactor. The separation of the heterogeneous catalyst from the reaction mixture is thus effected mechanically and directly within the reaction zone.

The separation of a homogeneous catalyst from a reaction mixture is, however, much more demanding, since the homogeneous catalyst is dissolved in the reaction mixture. A simple mechanical separation is therefore not an option. Consequently, in the case of homogeneously catalysed processes, the catalyst is withdrawn from the reaction zone dissolved in the reaction mixture and is separated from the reaction mixture in a separate step. The catalyst is generally separated outside the reaction zone. The separated catalyst is recycled into the reaction zone.

Particular technical problems occur in the removal of catalyst systems which are particularly sensitive to changes in state and consequently have to be separated off in a particularly gentle manner.

For instance, some reactions are conducted in the presence of highly effective but highly sensitive homogeneous catalyst systems, for example organometallic complexes. The metal present in the catalyst system can be separated off virtually completely and retained in the plant. However, the complex is destroyed easily in the event of improper separation, and so the retained catalyst becomes inactive and hence unusable.

The separation of homogeneously dissolved catalyst systems from reaction mixtures with minimum loss of material and activity is therefore a demanding task in chemical engineering.

This task arises especially in the field of rhodium-catalysed hydroformylation.

Hydroformylation—also called the oxo process—enables reaction of olefins (alkenes) with synthesis gas (mixture of carbon monoxide and hydrogen) to give aldehydes. The aldehydes obtained then correspondingly have one carbon atom more than the olefins used. Subsequent hydrogenation of the aldehydes gives rise to alcohols, which are also called "oxo alcohols" because of their genesis.

In principle, all ethylenically unsaturated compounds are amenable to hydroformylation, but in practice the substrates used in the hydroformylation are usually those olefins having two to 20 carbon atoms. Since alcohols obtainable by hydroformylation and hydrogenation have various possible uses—for instance as plasticizers for PVC, as detergents in washing compositions and as odourants—hydroformylation is practised on an industrial scale.

Important criteria for distinction of industrial hydroformylation processes are, as well as the substrate used, the catalyst system, the phase division in the reactor and the technique for discharge of the reaction products from the reactor. A further aspect of industrial relevance is the number of reaction stages conducted.

In industry, either cobalt- or rhodium-based catalyst systems are used, the latter being complexed with an organophosphorus compound as ligand. In general, phosphine, phosphite or phosphoramidite compounds are used as ligand. These catalyst systems are all present in the form of a homogeneous catalyst dissolved in the reaction mixture.

The hydroformylation reaction is usually conducted in biphasic mode, with a liquid phase comprising the olefins, the dissolved catalyst and the products, and a gas phase which is formed essentially by synthesis gas. The products of value are then either drawn off from the reactor in liquid form ("liquid recycle") or discharged with the synthesis gas in gaseous form ("gas recycle"). A special case is the Ruhrchemie/Rhône-Poulenc process, in which the catalyst is present in an aqueous phase.

Some hydroformylation processes are also conducted in the presence of a solvent. These are, for example, alkanes present in the starting mixture.

Since the invention is concerned essentially with separation, especially with the separation of the catalyst system from a reaction mixture which stems from a homogeneously catalysed reaction such as, more particularly, a hydroformylation, reference is made to the extensive prior art with regard to the chemistry and reaction technology of hydroformylation. It is worth reading the following in particular:

Falbe, Jürgen: New Syntheses with Carbon Monoxide. Springer, 1980 (standard work relating to hydroformylation)

Pruett, Roy L.: Hydroformylation. Advances in Organometallic Chemistry. Vol. 17, pages 1 to 60, 1979 (review article)

Frohning, Carl D. and Kohlpaintner, Christian W.: Hydroformylation (Oxo Synthesis, Roelen Reaction). Applied homogeneous catalysis with organometallic compounds. Wiley, 1996, pages 29 to 104 (review article)

Van Leeuwen, Piet W. N. M and Claver, Carmen (Edit.): Rhodium Catalyzed Hydroformylation. Catalysis by Metal Complexes. Volume 22. Kluwer, 2000 (Monograph relating to Rh-catalysed hydroformylation. Emphasis on chemistry, but chemical engineering aspects are also discussed.)

R. Franke, D. Selent and A. Börner: "Applied Hydroformylation", Chem. Rev., 2012, DOI:10.1021/cr3001803 (overview of the current state of research).

A key factor for a successful, industrial-scale performance of Rh-based, homogeneously catalysed hydroformylations is the control of the catalyst separation.

One reason for this is that Rh is a very expensive noble metal, the loss of which should be avoided if possible. For this reason, the rhodium has to be separated substantially completely from the product stream and recovered. Since the Rh concentration in typical hydroformylation reactions is only 20 to 100 ppm and a typical "world scale" oxo process plant achieves an annual output of 200 000 tonnes, it is necessary to use separation apparatuses that firstly allow a large throughput and secondly reliably separate out the Rh, which is present only in small amounts. An additional complicating factor is that the catalyst complexes used are sensitive to changes in parameters (for example changing temperature and/or change in the partial CO pressure in the reaction mixture). If such a change occurs, the result may be deactivation of the catalyst complex, irreversibly in the worst case. The organophosphorus complexes which may be part of the catalyst complexes as ligands are not of unlimited stability either; for example, they can be decomposed by moisture, ingress of oxygen or excessively high temperatures, which likewise results in deactivation of the catalyst. In the best case, a deactivated catalyst can be reactivated only in a costly and inconvenient manner. The catalyst therefore has to be separated off in a particularly gentle manner. A further important development aim is the energy efficiency of the separating operations.

Membrane separation technology is an option for separation of homogeneous catalyst systems, since it consumes less thermal energy and is able to protect the catalyst:

Details of the possible uses of membrane technology for workup of hydroformylation mixtures are given by Priske, M. et al.: Reaction integrated separation of homogeneous catalysts in the hydroformylation of higher olefins by means of organophilic nanofiltration. Journal of Membrane Science, Volume 360, Issues 1-2, 15 Sep. 2010, Pages 77-83; doi:10.1016/j.memsci.2010.05.002.

The problem of the catalyst being deactivated while being separated off with a membrane was solved by the method described in EP 1 931 472 B1 for workup of hydroformylation mixtures, in which a particular partial carbon monoxide pressure is maintained in the feed, in the permeate and also in the retentate of the membrane. It is thus possible for the first time to use membrane technology effectively in industrial hydroformylation. A multistage membrane separation is not apparent here: thus, FIG. 3 of EP 1 931 472 B1 shows catalyst separation with the aid of two series-connected nanofiltrations. Since, however, a thermal removal of products by means of a thin-film evaporator is provided between the two nanofiltrations, the two nanofiltrations do not form a membrane cascade.

A further membrane-supported method for catalyst separation from homogeneously catalysed reactions such as hydroformylation in particular is known from WO 2013/034690 A1. The one-stage membrane technique disclosed therein is designed specially for the requirements of a jet loop reactor utilized as the reaction zone.

A membrane-supported separation of homogeneous catalyst out of hydroformylation mixtures is also described in the as yet unpublished German patent application DE 10 2012 223 572 A1.

Although several nanofiltrations are provided within one plant, the individual nanofiltrations are each assigned to one reactor in a reactor cascade. The nanofiltrations themselves likewise do not constitute a membrane cascade.

The same applies to DE 10 2013 208 759 A1, likewise as yet unpublished, which is concerned, inter alia, with the regulation of separation temperature and the retention of a membrane separation unit.

Finally, DE 10 2013 203 117 A1, likewise as yet unpublished, describes the use of a stripping cascade and an enriching cascade for catalyst separation and high boiler discharge from a homogeneously catalysed hydroformylation. Details of the temperature regime within the membrane cascade are not discussed.

Schmidt et al. likewise describe, in the journal Computer Aided Chemical Engineering volume 30, (2012), p. 727-731, the use of membrane cascades in hydroformylation.

Even though the prior art has already described measures for separating homogeneous catalyst systems out of the reaction mixtures, there is still the problem of availability of effective materials at acceptable prices.

Although there exist materials that are able to retain the homogeneously dissolved catalyst system, the retention is comparatively low, and so a correspondingly large membrane area has to be provided. This is all the more true when very large amounts of composition of matter are to be separated, for instance in the case of catalyst separation in a world-scale oxo process plant. The massive membrane areas required for this purpose significantly increase the capital costs, and so the membrane-supported catalyst separation is not always economically viable compared to a conventional thermal separation.

In the light of this prior art, the problem addressed by the invention is therefore that of specifying a membrane-based process for separating compositions of matter, which has a minimum membrane area requirement and nevertheless fulfils the separation task and separation performance required.

BRIEF DESCRIPTION OF THE DRAWINGS

Further features and advantages of the invention can be ascertained from the following detailed description that is provided in connection with the drawings described below.

This problem is solved by the use of a membrane cascade with falling separation temperature.

The invention therefore provides a process for separating a composition of matter with the aid of a membrane cascade having at least two stages, in which a separation is effected in each stage at at least one membrane at a separation temperature set for the particular stage, in which the particular separation temperature falls from stage to stage in the direction of the incoming composition of matter.

The invention is based on the surprising finding that the area of a membrane cascade—and hence the requirement thereof for separation-active membrane material—can be optimized while retaining the required separation performance (retention and volume flow rate of the feed to be processed) when the separation temperature within the cascade is lowered from stage to stage.

This finding is surprising in that the same separation temperature was always maintained within known membrane cascades:

This is because, if the customary heat losses are neglected, a conventional membrane cascade works isothermally. With the setting of the temperature of the feed to the membrane cascade, therefore, the separation temperature has been preset identically for all the stages.

In contrast, the invention teaches the setting of the separation temperature within the cascade in a controlled and separate manner for each individual stage, in such a way that the separation temperature falls downstream from stage to stage.

The invention makes use of the observation that the retention of the individual membrane separation stage is dependent on the separation temperature of this stage: this is because it is the case in principle that retention of the membrane rises with falling temperature. With rising retention, the permeate flow rate also becomes smaller, which enables a smaller membrane area within this stage.

This means that the total membrane area of a cascade can be optimized by setting the retention in the first stage at a comparatively low level, but correspondingly increasing it from stage to stage by lowering the temperature. The result of this is that the membranes become more impermeable from stage to stage. The resultant decrease in volume flow rates of the permeate can be utilized to lower the membrane areas overall.

However, this does not mean that the membrane area falls from stage to stage; on the contrary, the membrane area can also increase again towards the end. The exact size of the particular membrane area within the stage is calculated by the membrane specialist on the basis of the particular separation task to be fulfilled. Corresponding calculation methods are described in the cited textbook by Melin/Rautenbach.

A crucial boundary condition in the optimization of the total membrane area is the falling separation temperature. This finding applies in principle to the separation of any compositions of matter by means of a membrane cascade, irrespective of the system and phase composition. It is merely necessary to use a membrane material suitable for the separation of the desired component. The term "membrane material" refers to the material of the separation-active layer of a membrane.

For separation of homogeneously dissolved catalyst systems from reaction mixtures, preference is given to using membranes having a separation-active layer of a material selected from cellulose acetate, cellulose triacetate, cellulose nitrate, regenerated cellulose, polyimides, polyamides, polyether ether ketones, sulphonated polyether ether ketones, aromatic polyamides, polyamide imides, polybenzimidazoles, polybenzimidazolones, polyacrylonitrile, polyaryl ether sulphones, polyesters, polycarbonates, polytetrafluoroethylene, polyvinylidene fluoride, polypropylene, terminally or laterally organomodified siloxane, polydimethylsiloxane, silicones, polyphosphazenes, polyphenyl sulphides, Nylon 6,6, polysulphones, polyanilines, polyurethanes, acrylonitrile/glycidyl methacrylate (PANGMA), polytrimethylsilylpropyne, polymethylpentyne, polyvinyitrimethylsilane, polyphenylene oxide, aluminas having various crystal structures, titanium oxides, silicon oxides, zirconium oxides, ceramic membranes hydrophobized with silanes, as described in EP 1 603 663 81, polymers having intrinsic microporosity (PIM) such as PIM-1 and others, as described, for example, in EP 0 781 166 and in "Membranes" by Cabasso, Encyclopedia of Polymer Science and Technology, John Wiley and Sons, New York, 1987.

The abovementioned substances may be present, especially in the separation-active layer, optionally in cross-linked form through addition of auxiliaries, or in the form of what are called mixed matrix membranes with fillers, for example carbon nanotubes, metal-organic frameworks or hollow spheres, and particles of inorganic oxides or inorganic fibres, for example ceramic fibres or glass fibres.

Particular preference is given to using membranes having, as a separation-active layer, a polymer layer of terminally or laterally organomodified siloxane, polydimethylsiloxane or polyimide, formed from polymers having intrinsic microporosity (PIM) such as PIM-1, or wherein the separation-active layer has been formed by means of a hydrophobized ceramic membrane. A detailed description of such membranes for use in high boiler discharge can be found in EP2401078A1.

Very particular preference is given to using membranes formed from terminally or laterally organomodified siloxanes or polydimethylsiloxanes. Membranes of this kind are commercially available.

As well as the abovementioned materials, the membranes may also include further materials. More particularly, the membranes may include support or carrier materials to which the separation-active layer has been applied. In such composite membranes, a support material is present as well as the actual membrane. A selection of support materials is described by EP0781166, to which reference is made explicitly.

A selection of commercially available solvents for stable membranes are the MPF and Selro series from Koch Membrane Systems, Inc., different types of Solsep BV, the Starmem™ series from Grace/UOP, the DuraMem™ and PuraMem™ series from Evonik Industries AG, the NanoPro series from AMS Technologies, the HITK-T1 from IKTS, and also oNF-1, oNF-2 and NC-1 from GMT Membrantechnik GmbH and the Inopor® nano products from Inopor GmbH.

As well as the membrane material, the design of the membrane modules is also of relevance for the separation performance of the individual stage. The membrane is preferably designed as a spiral-wound element. Alternatively, it is also possible to use membranes, for example, in the form of plate modules, cushion modules, tube modules, pipe modules, capillary modules, hollow fibre modules or membrane discs.

Another crucial factor for the required membrane area to fulfil the separation task is the connection of the stages within the cascade:

This is because the membrane cascade is preferably an enriching cascade, i.e. a connection arrangement in which the individual stages are connected in series in the direction of permeate flow. The inventive concept works particularly well in the case of an enriching cascade, since the connection is effected in the direction of falling permeate flow, which allows the optimization of the overall membrane area to be particularly successful.

For the same reason, the enriching cascade is designed such that the resulting permeate has permeated through all the stages of the membrane cascade.

In order to improve the retention of the membrane cascade overall, one option is to recycle the retentate from at least one stage for the purpose of a further separation step. The retentate is accordingly recycled into the feed to the same stage from which the retentate has been recycled and/or into the feed to another stage counter to the direction of the incoming composition of matter. The recycled retentate is always mixed with a stream having a lower workup level.

A membrane cascade necessarily has at least two stages. However, a three- or four-stage membrane cascade may also be economically viable.

As already mentioned above, a membrane cascade is to be regarded as isothermal if no further technical measures are provided for temperature control within the membrane. The heat losses that naturally occur within the cascade in the permeate direction will generally not be sufficient to attain optimal separation temperatures in the individual stages. For this reason, it is appropriate for each stage of the membrane cascade to have a dedicated temperature control unit which sets the temperature of the feed to the particular stage to the particular temperature set for that stage. The temperature control unit need not necessarily be arranged within the membrane cascade, but may also be outside the latter. Thus, the composition of matter to be separated may especially be provided already having the temperature required for the first stage.

The temperature control unit in the simplest case is a cooler, since the temperature is lowered in each case in the direction of permeate flow. The arrangement of a cooler within a membrane cascade does of course mean that the membrane cascade has a thermal energy requirement in the form of cooling coolant. The operating costs for an inventive membrane cascade may therefore be higher than those of the conventional membrane cascade which merely consumes mechanical power. However, these higher operating costs can be balanced out again by lower capital costs or improved retention and hence better product purity, such that the inventive membrane cascade is more economically viable than conventional plants in spite of its coolant requirement.

As already mentioned, the process according to the invention is suitable in principle for separation of any compositions of matter. More preferably, however, it is used to separate off homogeneously dissolved catalyst systems, since it has been found to be particularly cost-efficient here. In a particularly preferred development of the invention, the composition of matter accordingly originates from a homogeneously catalysed chemical reaction, and it comprises at least one product of the reaction, at least one reactant unconverted in the reaction, and the catalyst system present in the reaction and/or at least one constituent and/or a degradation product thereof, the catalyst system or constituent thereof or degradation product thereof being dissolved in the composition of matter.

The reaction is preferably a hydroformylation. Accordingly, the product is an aldehyde or an alcohol, and the reactants are olefins and synthesis gas. The catalyst system is preferably an organometallic complex of rhodium (although complexes of the other transition metals from groups 7-9 of the Periodic Table of the Elements may also find use) which may contain, for example, an organophosphorus compound as ligands. In this specific field of use, the process according to the invention was usable in a particularly advantageous manner.

The invention also provides a membrane cascade intended for the inventive separation of a composition of matter. The membrane cascade is especially designed as an enriching cascade comprising at least two stages arranged in succession, in which each stage has a dedicated temperature control unit, by means of which the temperature of the feed to the particular stage can be set to a particular separation temperature set for that stage, and in which the particular separation temperatures are set such that the particular separation temperature—viewed in the direction of the incoming gas mixture—falls from stage to stage.

The invention also provides for the use of this membrane cascade for separation of a dissolved catalyst complex and/or at least one constituent and/or a degradation product thereof from a composition of matter originating from a chemical reaction homogeneously catalysed in the presence of a catalyst complex.

Since the process according to the invention is preferably used to separate off the catalyst within homogeneously catalysed industrial hydroformylation, this invention also provides a process for hydroformylating ethylenically unsaturated compounds by reaction with carbon monoxide and hydrogen in the presence of a catalyst system comprising a dissolved metal complex of a metal of the eighth transition group of the Periodic Table of the Elements with at least one organophosphorus compound as ligands, in which a reaction mixture comprising not only hydroformylation products hut also unconverted reactants and the catalyst system or at least constituents and/or degradation products thereof in dissolved form is obtained, wherein the reaction mixture is sent to a catalyst separation in which the catalyst system or constituents and/or degradation products thereof are separated from the reaction mixture at least partly by means of membrane technology for the purpose of recycling into the hydroformylation, which the catalyst separation comprises a membrane cascade having at least two stages, in which a separation is effected in each stage at at least one membrane at a separation temperature set for that particular stage, the particular separation temperature—viewed in the direction of the incoming reaction mixture—falling from stage to stage.

Figure 4:
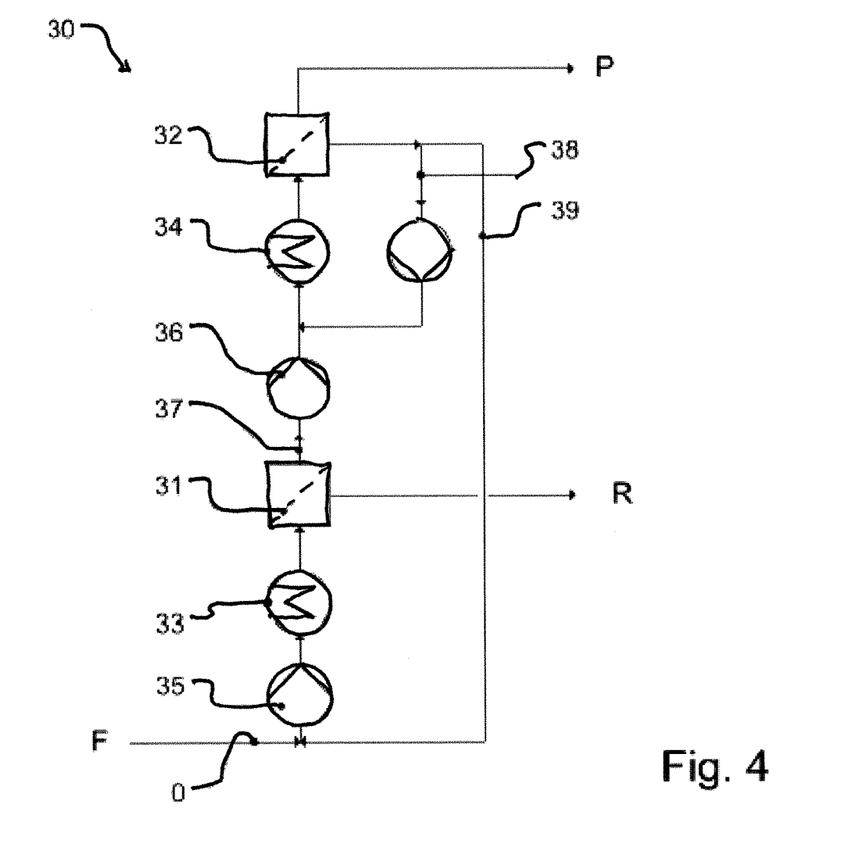
FIG. 4 shows a two-stage membrane cascade according to one embodiment of the present invention.
Figure 5:
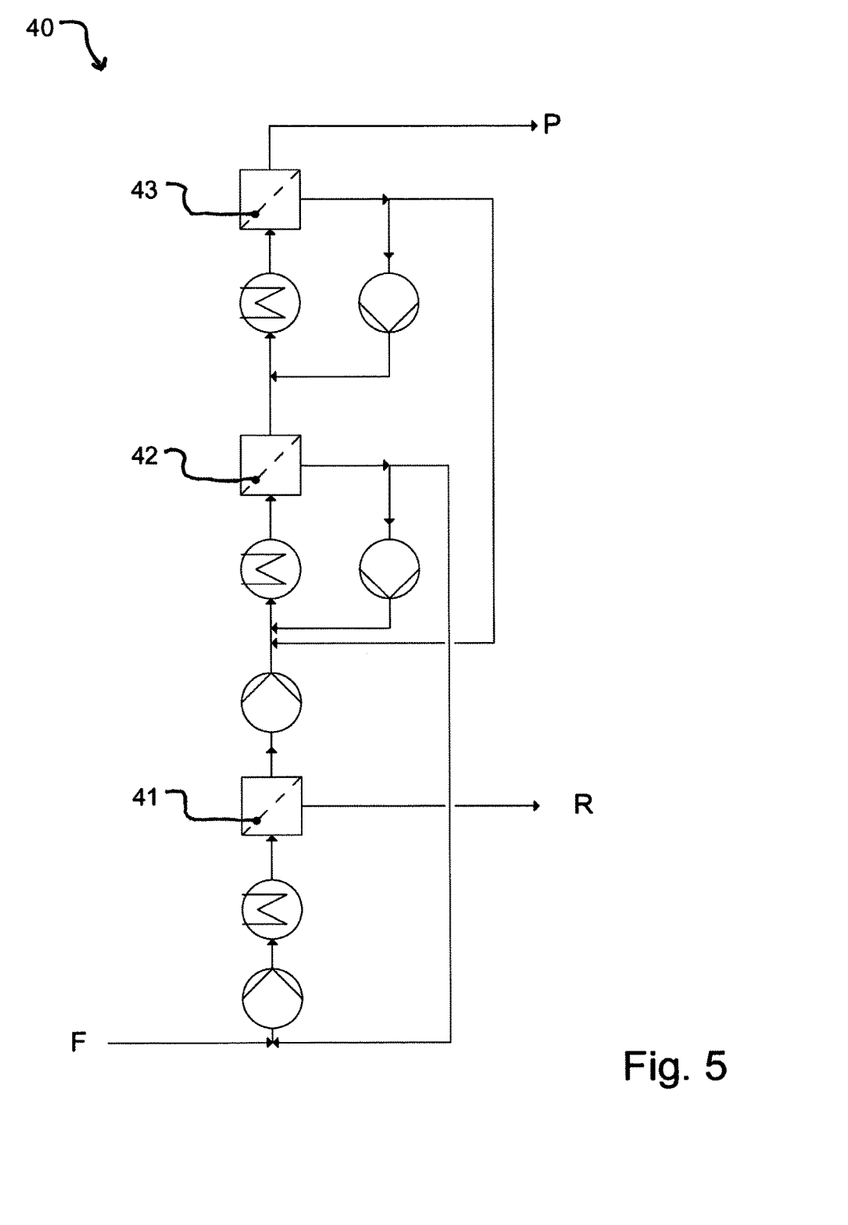
FIG. 5 shows a three-stage membrane cascade according to another embodiment of the present invention.
Figure 6:
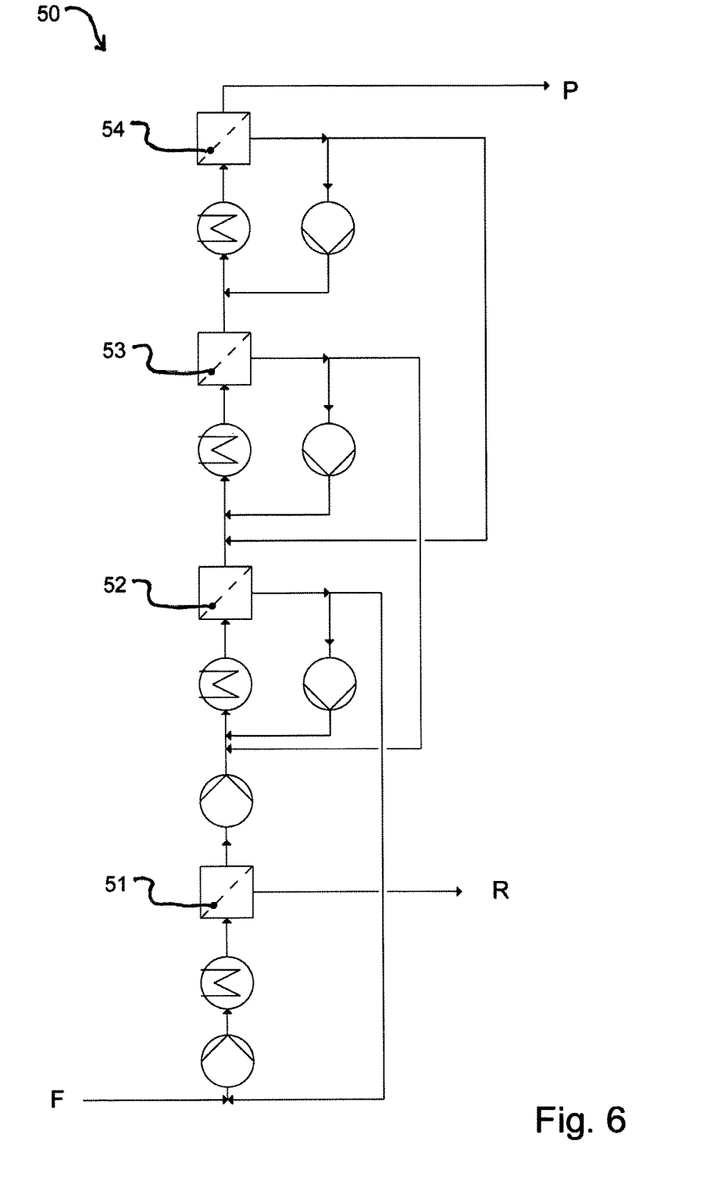
FIG. 6 shows a four-stage membrane cascade according to still another embodiment of the present invention.
Figure 7:
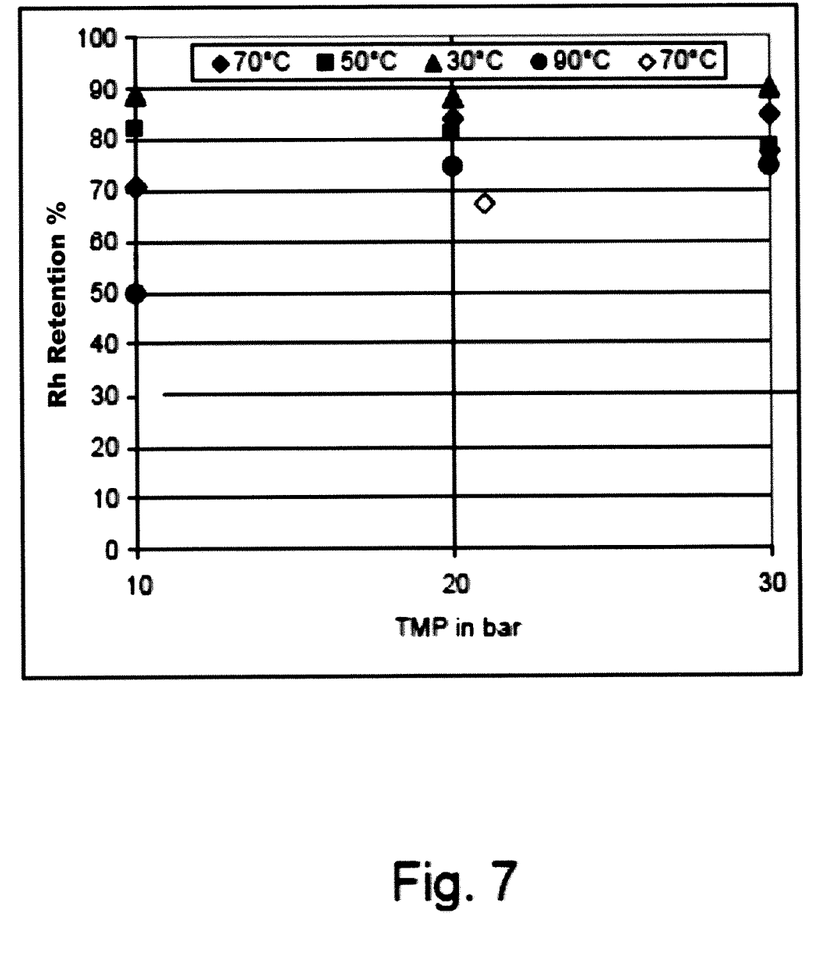
FIG. 7 is a graph showing the dependence of retention on temperature.
Figure 8:
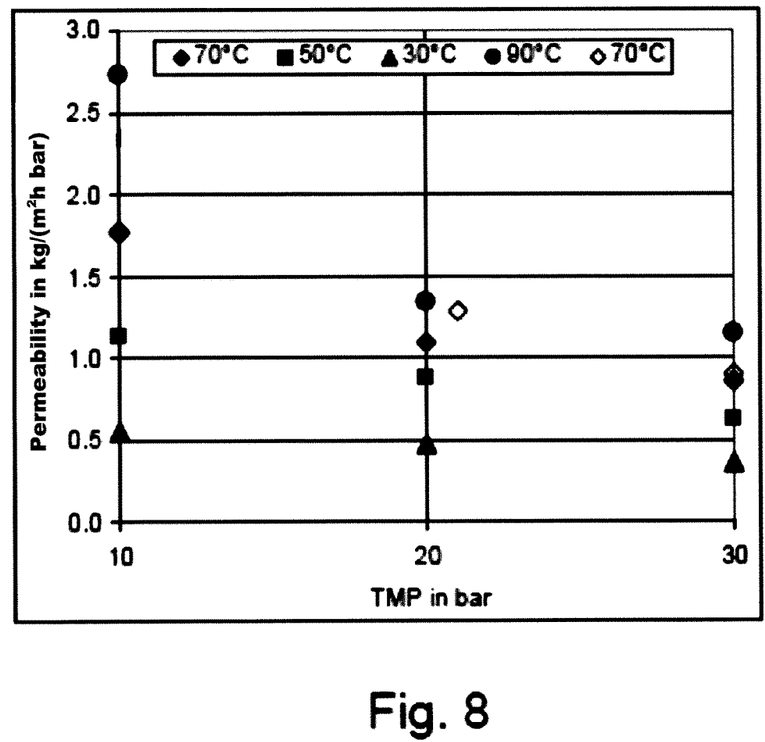
FIG. 8 is a graph showing the dependence of permeability on temperature.

The invention will now be illustrated in detail by working examples. The figures show:

FIG. 4: two-stage membrane cascade (inventive);
FIG. 5: three-stage membrane cascade (inventive);
FIG. 6: four-stage membrane cascade (inventive);
FIG. 7: dependence of permeability on temperature;
FIG. 8: dependence of retention on temperature.

FIG. 4 shows a first embodiment of the invention in the form of a two-stage enriching cascade suitable for performing a process according to the invention. The feed F of the two-stage enriching cascade 30 is the output from a homogeneously catalysed hydroformylation. More specifically, $C_5$ olefins (pentenes) are reacted here with hydrogen and carbon monoxide in the presence of a rhodium-phosphite catalyst system to give hexanals.

The reaction output is a mixture of the two hexanals formed (n-hexanal and 2-methylpentanal) in which the homogeneously dissolved catalyst is present in a concentration of 37 ppm (based on mass). The conversion of pentenes is 99% and the regioselectivity for the linear product is 67%. This corresponds to a reaction at a temperature of 100° C., a pressure of 40 bar, a $CO/H_2$ ratio of 1, and a residence time in the reactor of 2 hours. The reaction output comprising the hexanals formed, unconverted pentenes, dissolved synthesis gas and the catalyst system are applied as feed F to the enriching cascade 30. If required, the reaction output can be degassed beforehand, in which case a residual amount of synthesis gas has to be maintained in the feed, in order to stabilize the organophosphorus ligand against deactivation.

The enriching cascade 30 has two stages 31 and 32. Each stage 31, 32 is formed by two series-connected membrane modules, but each should be regarded as a single membrane. The membrane material used was a silane-modified ceramic based on a $ZrO_2$ support and a pore size of 3 nm; the module design selected was tube modules of the Inopor M07-19-41-L type having a length of 40 inches and an area of 2.54 $m^2$.

The special feature of the inventive enriching cascade 30 is that each membrane stage, in the feed, has a dedicated temperature control unit 33, 34 for the particular stage 31, 32. The temperature control units 33, 34 are thermostatically regulated coolers which set the feed to the particular stages 31, 32 to a separation temperature set for that particular stage. The separation temperatures of the stages are selected such that the separation temperature falls in the direction of the incoming feed F:

Thus, the first temperature control unit 33 sets the separation temperature of the first stage 31 to 43.4° C., while the temperature control unit 34 fixes the separation temperature of the second stage 32 at 30° C.

The transmembrane pressure set in each stage is 60 bar, for which a pump 35, 36 is provided in the feed to each stage.

The pump in the first stage 35 conveys the feed F through the first temperature control unit 33, such that it arrives at the first stage 31. A separation takes place therein, to the effect that the products and reactants present in the reaction mixture pass through the membranes preferentially, i.e. more quickly, and accordingly accumulate in the permeate 37 from the first stage. The catalyst system, in contrast, is not able to pass through the membrane as quickly, and so it accumulates in the retentate from the first stage, which is drawn off as resulting retentate R from the membrane cascade 30 and conducted back into the hydroformylation reactor.

No membrane is entirely impermeable to the catalyst system. Consequently, the permeate 37 from the first stage 31 also comprises rhodium and organophosphorus ligand or degradation products thereof. To separate off further catalyst complex, the permeate 37 from the first stage 31 is applied as feed to the second stage 32. To compensate for the pressure drop experienced, which is of the magnitude of the transmembrane pressure that acts over the first stage, the pressure of the permeate 37 is increased again with the aid of the pump 36. Then cooling takes place in the temperature control unit 34, in order that a membrane separation can again take place in the second stage 32 at the same pressure level but at a lower separation temperature.

The permeate from the second stage 32 is discharged as resulting permeate P from the two-stage enriching cascade 30. It is very substantially free of the catalyst system or any degradation products thereof. It can then be sent to a distillative product separation in which the actual target product (hexanal) can be separated from high boilers formed in side reactions.

Meanwhile, the retentate 38 from the second stage 32 is recycled within the membrane cascade 30, once via a recycling loop within the second stage 32, for which a recycling pump is arranged within the recycling loop 38, and via a second recycling loop 39, which recycles the retentate from the second stage 32 in the feed to the first stage 31. The second recycling loop 39 does not need a dedicated pump, since the pump 35 upstream of the first stage sucks in the recycled retentate from the second stage 32 as well.

The value $RR_{int}$ is set to 12.1 kmol/kmol in the second stage and to 10.5 kmol/kmol in the first stage. This means that (based on molar amounts) 12.1 and 10.5 times more, respectively, is recycled internally (e.g. stream 38) than is conveyed externally into the stage beneath (e.g. stream 39, or to the global retentate in the first stage).

Because of the falling separation temperature from 43° C. in the first stage to 30° C. in the second stage, the retention of the first stage is lower than that of the second stage. In the first stage the retention is 88.7%, while the retention in the second stage is 91.3%.

Because of the lower retention, the permeate flow in the first stage 31 (i.e. the volume flow rate of the permeate 37) is much greater than the permeate flow of the second stage 32 (i.e. the volume flow rate of the resulting permeate P). Accordingly, the membrane area in the first stage is much greater at 163 m² than that in second stage at 81.4 m².

Overall, the two-stage membrane cascade 30 shown in FIG. 4 requires a total membrane area of 244.4 m². Thus, an overall retention based on the catalyst complex of 98.33% is achieved, This means that 98.33% of the catalyst introduced with the feed can be recovered and leaves the membrane cascade 30 again via the resulting retentate R in the direction of the reactor. The remaining 1.67% of the catalyst system is lost with the permeate P.

In order to reduce catalyst losses by the resulting permeate P, the catalyst retention has to be enhanced further. One option for this purpose is a three-stage enriching cascade as shown, for example, in FIG. 5.

As its name suggests, the three-stage enriching cascade 40 has three stages 41, 42, 43, which are connected to one another analogously to the two-stage enriching cascade 30 shown in FIG. 4. The resulting retentate R from the cascade 40 is drawn off from the first stage 41. The resulting permeate P permeates through all the stages 41, 42 and 43. The retentates from the second and third stages are recycled, partly into the feed to the same stage and partly into the feed to the preceding stage. The value $RR_{int}$ is 0.5 kmol/kmol in the first stage, 5.1 kmol/kmol in the second stage and 16.6 kmol/kmol in the third stage.

The membrane material used is homogeneous and is the same as in the two-stage enriching cascade 30 shown in FIG. 4. The same transmembrane pressure of 60 bar was also selected. The separation temperature decreases again in the direction of permeate flow from 88.9° C. in the first stage 41, through 73.1° C. in the second stage 42, down to 30.17° C. in the third stage 43. The membrane area selected in the first stage was 64.5 m²; provided by two series-connected "Inopor M07-19-41-L" modules having a length of 40 inches and an area of 2.54 m² each. The second stage 42 has a membrane area of 61 m², likewise realized via two series-connected membrane modules. In the third and last stage 43, however, the membrane area was raised to 81.2 m², provided by a single membrane. Overall, the three-stage enriching cascade requires 206.7 m² of costly membrane material. However, the retention thereof, based on the catalyst complex, is 99.24%. Compared to the two-stage enriching cascade 30, the three-stage enriching cascade therefore achieves better retention with a smaller membrane area. The three-stage embodiment shown in FIG. 5 is therefore much more effective than the two-stage membrane cascade shown in FIG. 4.

In order to further enhance the retention of the membrane cascade, a four-stage system may be provided. FIG. 6 shows a corresponding four-stage enriching cascade 50. The connection thereof is analogous to that of the three-stage enriching cascade 40 and two-stage enriching cascade 30. The composition of the feed F and the membrane material and the module design correspond to the membrane cascades from FIGS. 4 and 5. The stages 51, 52, 53 and 54 were selected as follows:

First stage 51: separation temperature 90° C., transmembrane pressure 60 bar, number of membranes 2, membrane area 53.2 m², $RR_{int}$ 0.3 kmol/kmol.

Second stage 52: separation temperature 85.5° C., transmembrane pressure 60 bar, number of membranes 2, membrane area 73.9 m², $RR_{int}$ 7.8 kmol/kmol.

Third stage 53: separation temperature 80.9° C., transmembrane pressure 60 bar, number of membranes 2, membrane area 66.5 m², $RR_{int}$ 4.8 kmol/kmol.

Fourth stage 54: separation temperature 63.9° C., transmembrane pressure 60 bar, number of membranes 2 having a total area of 53.3 m², $RR_{int}$ 6.1 kmol/kmol.

The four-stage membrane cascade 50 achieves an overall retention of 99.5% with a total membrane area of 245.9 m². The membrane area is thus almost exactly as high as that in the two-stage enriching cascade 30 from FIG. 4, but the retention is much better.

For comparison, the three inventive enriching cascades 30, 40 and 50 were operated unchanged, but at a homogeneous separation temperature within the cascade. The results are shown in Table 1.

| Number of stages | Isothermal temperature set [° C.] | Equivalent total membrane area [m$^2$] | Catalyst retention with isothermal temperature control [%] | Comparative catalyst retention value with non-isothermal control [%] |
|---|---|---|---|---|
| 2 | 38.64 | 244.4 | 97.91 | 98.33 |
| 3 | 73.88 | 206.7 | 98.08 | 99.24 |
| 4 | 80.44 | 245.9 | 99.41 | 99.50 |

The comparison shows that the inventive membrane cascades 30, 40 and 50, with the same membrane area, give higher retention than the cascades operated isothermally, contrary to the teaching of the invention.

This means, conversely, that the same retention can be achieved with a smaller membrane area.

FIGS. 7 and 8 show the effect of the temperature dependence of the retention and permeability, utilized in accordance with the invention. FIGS. 7 and 8 show the results with respect to catalyst retention (Rh retention) and permeability. The lower the temperature, the higher the retention and hence the lower the permeability.

Figure 9:
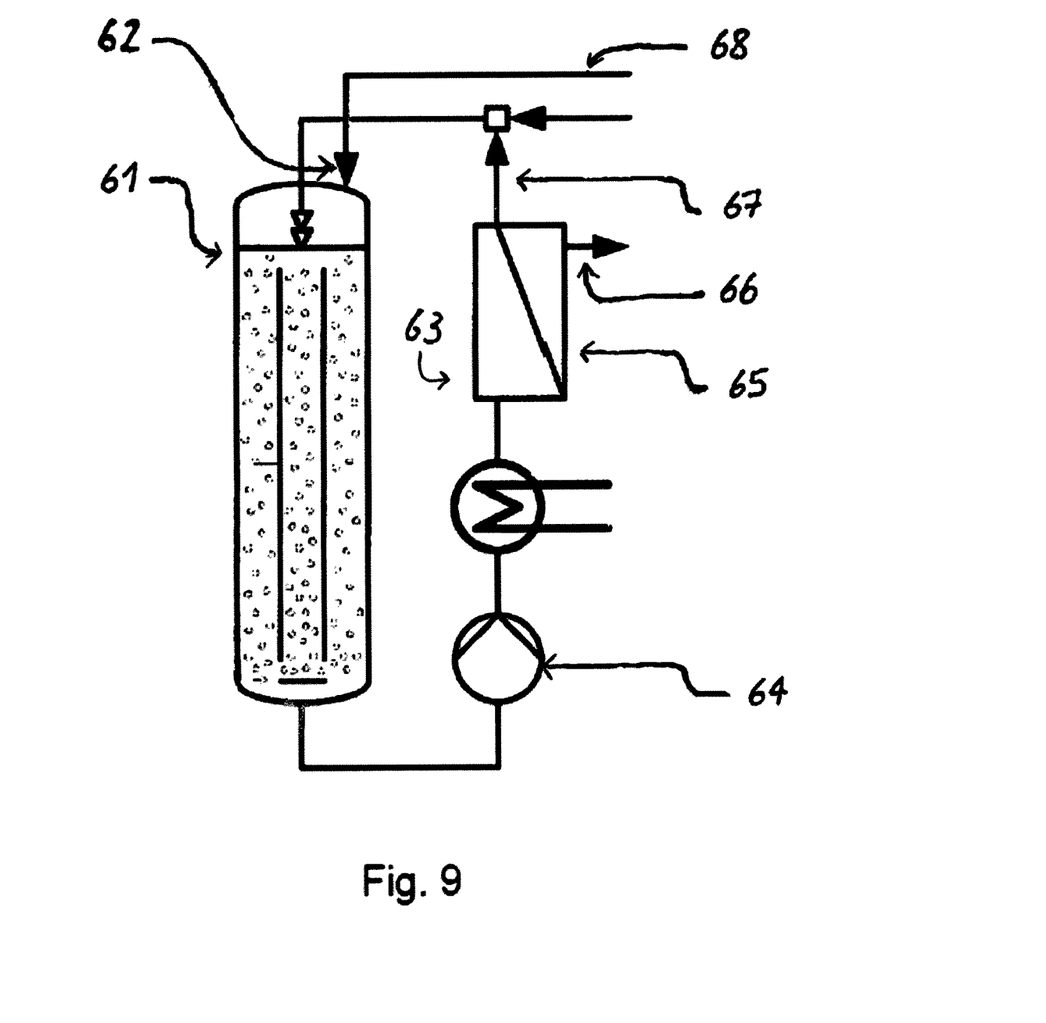
FIG. 9 shows a membrane separation with a jet loop reactor according to one embodiment of the present invention.

In an experimental plant with a jet loop reactor (61), shown in FIG. 9, hydroformylation reactions of 1-pentene (68) with synthesis gas (62) were conducted to give the corresponding aldehyde isomers. In the liquid circulation system (63) driven by a peripheral wheel pump (64), the catalyst-ligand system was separated off and recycled by means of a membrane separation stage (65) for continuous reuse of the catalyst-ligand system in the hydroformylation reaction in the jet loop reactor (61).

For the reaction, the reactor was supplied continuously with 1-pentene (68) with exclusion of oxygen, in accordance with the removal of reaction product via the permeate from the membrane separation stage. The catalyst precursor was rhodium acetylacetonato dicarbonyl (CAS No. 14847-82-9). The ligand used was Alkanox P-24 (CAS No. 26741-53-7). The rhodium concentration and the ligand concentration in the loop reactor were kept constant at 10 mg/kg and 1170 mg/kg respectively by continuous metered addition. The reaction was conducted under synthesis gas pressure of 50 bar (CO/H$_2$, mass ratio 1:1), at 110° C.

The reaction product was conducted continuously through a membrane separation stage (65) designed as a one-stage nanofiltration membrane. The transmembrane pressure required is built up through the reactor pressure and a regulated permeate-side pressure. The desired crossflow of 500 km/h over the high-pressure side of the membrane is set by means of the peripheral wheel pump (64).

In the membrane module of the membrane separation stage (65) was installed a prototype of a membrane hydrophobized by silanization, in the form of a single-channel tube from the Fraunhofer Institute for Ceramic Technologies and Systems KIS. The carrier consisted of Al$_2$O$_3$ having a median pore size of 3 µm and a hydrophobized membrane layer based on a ZrO$_2$ layer having a median pore diameter of 3 nm.

With a channel length of 500 mm and an internal diameter of 7 mm, the active membrane area is about 100 cm$^2$. The membrane crossflow was 4.4 m/s. Membrane temperatures of 30 to 90° C. were set. To stabilize the catalyst-ligand complex, a synthesis gas pressure (CO/H$_2$, mass ratio 1:1) of 10 bar was maintained on the permeate side, as a result of which a transmembrane pressure of 10 to 30 bar was set at a retentate-side pressure of 20 to 40 bar.

In the membrane separation stage, permeate (66) consisting predominantly of reaction product was withdrawn from the system through the membrane. The catalyst and the Alkanox ligand were very substantially retained by the membrane and accumulated in the retentate (67). The retentate (67) was conducted continuously back into the jet loop reactor (61).

The process sequence was evaluated using measurement and analysis data which were obtained by gas chromatography analysis, HPLC analysis, atomic absorption spectrometry and optical emission spectrometry with inductively coupled high-frequency plasma. The reaction was examined with regard to the conversion of 1-pentene and the yield of and selectivity for aldehyde. The membrane separation stage (65) was examined with regard to permeate flow and retention of rhodium. The composition of the reaction output was as follows:

| 1-Penten | 2-M.pentanal | Hexanal | Remainder |
|---|---|---|---|
| 3.7% | 53.3% | 42.2% | 0.8% |

LIST OF REFERENCE NUMERALS 0 composition of matter
1 membrane
F feed
P (resulting) permeate
R (resulting) retentate
10 enriching cascade (prior art)
11 first stage of the enriching cascade
12 second stage of the enriching cascade
13 conveying pump for the first stage
14 retentate from the first stage
15 permeate from the first stage
16 high-pressure pump
17 retentate from the second stage
18 permeate from the second stage
20 stripping cascade (prior art)
21 first stage of the stripping cascade
22 second stage of the stripping cascade
23 pressure-increasing pump
24 retentate from the first stage
25 permeate from the first stage
26 permeate from the second stage
27 retentate from the second stage
30 two-stage enriching cascade
31 first stage of the enriching cascade
32 second stage of the enriching cascade
33 first temperature control unit
34 second temperature control unit
35 pump for the first stage
36 pump for the second stage
37 permeate from the first stage
38 recycle loop upstream of the second stage
39 recycle loop upstream of the first stage
40 three-stage enriching cascade 41 first stage of the enriching cascade
42 second stage of the enriching cascade
43 third stage of the enriching cascade
50 four-stage enriching cascade
51 first stage of the enriching cascade
52 second stage of the enriching cascade
53 third stage of the enriching cascade
54 fourth stage of the enriching cascade
61 jet loop reactor
62 synthesis gas
63 liquid circulation system
64 peripheral wheel pump
65 membrane separation stage
66 permeate
67 retentate
68 1-pentene

The invention claimed is:

1. Process for separating a composition of matter with the aid of a membrane cascade having at least two stages, in which a separation is effected in each stage at at least one membrane at a separation temperature set for the particular stage, wherein the particular separation temperature falls from stage to stage in the direction of the incoming composition of matter, wherein each stage of the membrane cascade has a dedicated temperature control unit which sets the temperature of the feed to the particular stage to the particular temperature set for that stage, and wherein the separation temperature of the final stage is at least 10 degrees lower than the separation temperature of the initial stage.

2. Process according to claim 1, wherein the membrane cascade is an enriching cascade.

3. Process according to claim 2, wherein the permeate that results from the membrane cascade has permeated through all the stages of the membrane cascade.

4. Process according to claim 2, wherein at least the retentate of one stage is recycled into the feed to the same stage and/or into the feed to another stage positioned counter to the direction of the incoming composition of matter.

5. Process according to claim 1, wherein the membrane cascade has exactly two or exactly three or exactly four stages.

6. Process according to claim 1, wherein at least one temperature control unit is a cooler.

7. Process according to claim 1, wherein the composition of matter originates from a homogeneously catalyzed chemical reaction, and in that it comprises at least one product of the reaction, at least one reactant unconverted in the reaction, and the catalyst system present in the reaction and/or at least one constituent and/or a degradation product thereof, the catalyst system or constituent thereof or degradation product thereof being dissolved in the composition of matter.

8. Process according to claim 7, wherein the reaction is a hydroformylation, the product being an aldehyde or an alcohol, the reactant being an olefin or synthesis gas, and the catalyst system being rhodium complexed with an organophosphorus complex.

9. Membrane cascade for separating a composition of matter, comprising at least two stages arranged in series, wherein each stage of the membrane cascade has a dedicated temperature control unit configured to set a separation temperature such that—viewed in the direction of the incoming composition of matter—the separation temperature falls from stage to stage, and wherein the separation temperature of the final stage is at least 10 degrees lower than the separation temperature of the initial stage.

10. The membrane cascade according to claim 9, configured for separation of a dissolved catalyst complex and/or at least one constituent and/or degradation product thereof from a composition of matter originating from a chemical reaction homogeneously catalysed in the presence of the catalyst complex.

11. Process for hydroformylating ethylenically unsaturated compounds by reaction with carbon monoxide and hydrogen in the presence of a catalyst system comprising a dissolved metal complex of a metal of the eighth transition group of the Periodic Table of the Elements with at least one organophosphorus compound as ligands, in which a reaction mixture comprising not only hydroformylation products but also unconverted reactants and the catalyst system or at least constituents and/or degradation products thereof in dissolved form is obtained, wherein the reaction mixture is sent to a catalyst separation in which the catalyst system or constituents and/or degradation products thereof are separated from the reaction mixture at least partly by means of membrane technology for the purpose of recycling into the hydroformylation, wherein the catalyst separation comprises a membrane cascade having at least two stages, in which a separation is effected in each stage at at least one membrane at a separation temperature set for that particular stage, the particular separation temperature falling from stage to stage—viewed in the direction of the incoming reaction mixture, and wherein the separation temperature of the final stage is at least 10 degrees lower than the separation temperature of the initial stage.

12. Process according to claim 3, wherein at least the retentate of one stage is recycled into the feed to the same stage and/or into the feed to another stage positioned counter to the direction of the incoming composition of matter.

13. The process of claim 1, wherein the pressure is the same at each stage of the membrane cascade.

14. The process of claim 11, wherein the pressure is the same at each stage of the membrane cascade.

15. The process of claim 11, wherein the catalyst separation results in a retention of the catalyst system of at least 98.33 percent.

16. The process of claim 11, wherein the membrane cascade has three stages and the catalyst separation results in a retention of the catalyst system of about 99.24 percent.

17. The process of claim 11, wherein the membrane cascade has four stages and the catalyst separation results in a retention of the catalyst system of about 99.50 percent.

* * * * *